United States Patent [19]

Van Acker et al.

[11] Patent Number: 4,942,597
[45] Date of Patent: Jul. 17, 1990

[54] X-RAY SCANNER COMPRISING A LINEAR ELECTRIC DRIVING MOTOR

[75] Inventors: Paul A. F. Van Acker; Alphonsus T. Van Der Velden, both of Eindhoven, Netherlands

[73] Assignee: U.S. Philips Corporation, New York, N.Y.

[21] Appl. No.: 907,692

[22] Filed: Sep. 15, 1986

[30] Foreign Application Priority Data

Sep. 17, 1985 [NL] Netherlands ............ 8502533

[51] Int. Cl.$^5$ ............................................. H05G 1/02
[52] U.S. Cl. ........................................ 378/197; 378/4; 378/15
[58] Field of Search ............ 378/4, 15, 20, 193, 378/197, 209; 310/268, 105, 305; 128/660

[56] References Cited

U.S. PATENT DOCUMENTS

| | | | |
|---|---|---|---|
| 2,454,364 | 11/1948 | Winther | 310/105 |
| 4,276,490 | 6/1981 | Saldinger | 310/156 |
| 4,397,032 | 8/1983 | Kuipers | 378/11 |
| 4,479,388 | 10/1984 | Matzuk | 128/660 |
| 4,618,789 | 10/1986 | Flisikowski | 310/27 |

FOREIGN PATENT DOCUMENTS 0004092  1/1979  Japan ..................................... 378/15

OTHER PUBLICATIONS

Deleroi, W. et al., "Lineaire Elektrische Machines", *PT Elektrotechniek/Elektronica*, vol. 37, No. 9, pp. 105–110 (1982).

Deleroi, W., "De Lineaire Inductiemotor", *PT Elektrotechniek/Elektronica*, vol. 37, No. 10, pp. 129–133 (1982).

Primary Examiner—Janice A. Howell
Assistant Examiner—John C. Freeman
Attorney, Agent, or Firm—Thomas A. Briody; Jack E. Haken; Jack D. Slobod

[57] ABSTRACT

In an X-ray scanner, the driving motor (10) for the X-ray source (4) with the detector (5) is in the form of a linear motor, which is preferably provided with two magnet poles (15), between which a metal disk (9) is moveable. The metal disk is connected to a supporting ring (7) for the source and the detector.

7 Claims, 1 Drawing Sheet

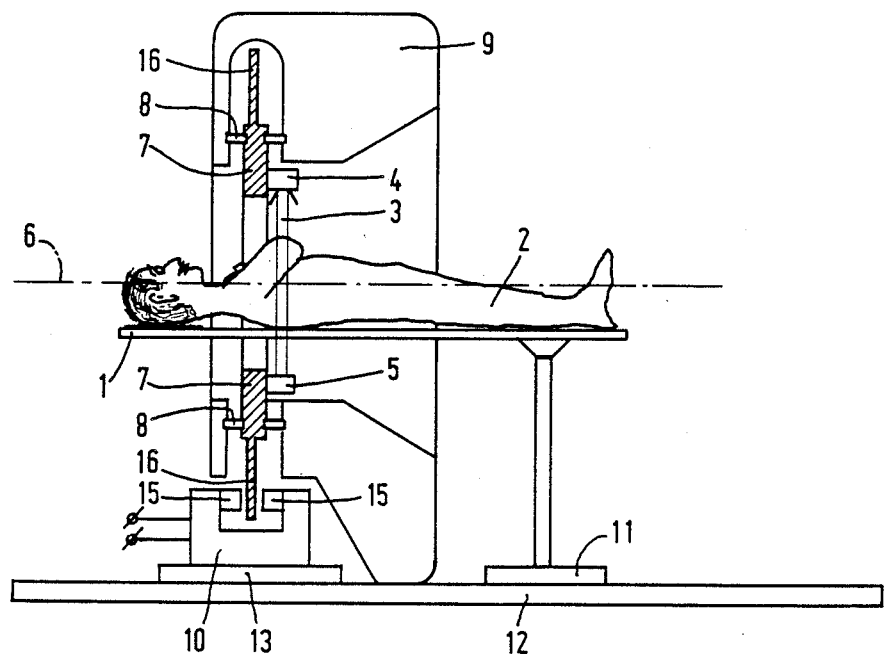

X-RAY SCANNER COMPRISING A LINEAR ELECTRIC DRIVING MOTOR

BACKGROUND OF THE INVENTION

The invention relates to an X-ray scanner comprising an X-ray source and an X-ray detector, which are driven together by a rotational driving system and are mounted in a support so as to be rotatable about an axis extending through an examination space.

Such an X-ray scanner is known from U.S. 4,397,032. In this case, the rotational driving system is provided with an alternating current motor driving through a gear wheel a ring which is mounted around the measuring space and to which the X-ray tube and the detector are secured. With the use of this driving mechanism, difficulties are met especially at high scanning speeds due to the fact that the drive produces disturbing vibrations in the scanner and the rotation is associated with a strongly increasing noise pollution.

SUMMARY OF THE INVENTION

It is an object of the invention to obviate these difficulties. For this purpose, in an X-ray scanner of the type described above, the rotational driving mechanism is provided with a linear electric driving motor.

Due to the fact that in an apparatus according to the invention the alternating current motor with the mechanical transmission system is replaced by a drive acting directly upon the supporting ring, a simple low-noise mechanism is obtained. Since the energy transmission between stator and motor is effected in this case without any contact, the transmission of disturbing vibrations from the drive to the apparatus is completely avoided.

In a preferred embodiment, the driving motor is provided with two magnet poles, which are mounted on a part of the support acting as a stator and which can be energized, for example, via a rotary field. The rotor is then constituted by a metal disk, which forms part of the support of the X-ray tube and the detector. By means of the driving force supplied via the magnet poles, the speed of rotation is adjustable with a sufficient accuracy by control of the supply of the motor. An extensive description of linear electric motors is given in PT Eleckrotechniek—Elektronica 37, 1982, No. 9, p. 105-133 by Deleroi and Hamels. The driving motor with the magnet poles may also be connected to a supporting plate for the scanner through a vibration-damping intermediate part.

BRIEF DESCRIPTION OF THE DRAWING

A few preferred embodiments according to the invention will now be described more fully with reference to the sole Figure of the drawing. The Figure is a partly cross-sectional, partly schematic view of an X-ray scanner according to the invention.

DESCRIPTION OF THE PREFERRED EMBODIMENTS

A patient 2 lying on an examination table 1 is irradiated by a flat fan-shaped X-ray beam 3 emitted by an X-ray source 4. Radiation transmitted by the patient is measured by means of an X-ray detector 5, which comprises a series of detector elements arranged along the arc of a circle.

The X-ray source 4 and the detector 5 are rotated together during an examination about an axis 6 directed transverse to the X-ray beam. By means of a computer, the density distribution of a patient in a cross-section irradiated by the flat beam is calculated from the detector signals. An accurate calculation can be carried out when the X-ray source 4 with the detector 5 is rotated through an angle of at least 360°.

For this purpose, the X-ray source and the detector are mounted on a ring 7, which is rotatably arranged in the a support 9 by means of one or more bearings 8. In order to displace the patient in axial direction, in order to choose another cross-section thereof to be irradiated, the patient table is mounted on a carriage 11, which can be translated with respect to a base plate 12.

A driving motor 10 according to the invention in the form of a linear electric motor is also mounted on the base plate in this case via a vibration-damping intermediate part 13. The driving motor may alternatively be secured directly to the base plate of the support, however, because it can operate completely free from vibrations. Vibrations in the motor may occur, for example, by a non-ideal supply thereof.

The motor comprises two magnet poles 15, which are mounted at a relative distance on either side of a disk 16 consisting of a conductive material, preferably aluminium. By energization of the magnet poles, the disk 16 situated locally between the magnet poles and hence the supporting ring 8 for the X-ray source and the detector are rotated in the support 9.

A comparatively high power is required to attain the desired speed of the ring 8 and with alternating movements this could be considered as a disadvantage. For a scanner, in which the ring 8 performs a continuous movement, this disadvantage is entirely eliminated because only a low power is required to maintain the continuous movement. If desired, several motors may be mounted around the circumference of the supporting ring, for example, for a quick start. With the electric rotary field to be applied, the speed of rotation can be controlled within narrow limits, for example, up to a continuous speed of 360°/sec.

Due to the fact that this driving mechanism does not comprise a mechanical transmission system, vibrations from the motor, if they might occur therein, are not transmitted to the scanner and the rotation will take place practically without any noise.

What is claimed is:

1. An X-ray scanner comprising an X-ray source and an X-ray detector, which are driven together by a rotational driving system and are mounted in a supporting ring so as to be rotatable about a shaft extending through an examination space, characterized in that the driving mechanism is provided with a linear electric driving motor and characterized in that a stator part of the linear motor is provided with two magnet poles, an electrically conducting annular disk for driving purposes is freely rotatable between said two magnet poles, wherein said annular disk is secured to the supporting ring for the X-ray source and the detector.

2. An X-ray scanner as claimed in claim 1, characterized in that the electrically conducting annular disk consists of aluminium.

3. An X-ray scanner as claimed in claim 2, characterized in that the electrically conducting annular disk forms part of the supporting ring which consists of aluminium.

4. An X-ray scanner as claimed in any one of the preceding claims, characterized in that the rotational driving system has means for continuously rotating the supporting ring at a speed of rotation of about one revolution per second.

5. An X-ray scanner comprising:
   a support;
   a ring rotatably mounted on the support for rotation around an axis;
   an X-ray source mounted on the ring;
   and X-ray detector mounted on the ring opposite the X-ray source;
   an electrically conductive annular disk affixed to the ring, said disk extending at least partly around the axis and extending radially with respect to the axis, said annular disk extending radially outward from the ring, said annular disk having first and second sides arranged axially opposite one another; and
   at least first and second magnetic poles affixed to the support, said first magnetic pole being arranged on the first side of the annular disk, said second magnetic pole being arranged on the second side of the annular disk opposite the first magnetic pole.

6. An X-ray scanner as claimed in claim 5, characterized in that:
   the first and second magnetic poles are arranged at a first angular position with respect to the axis; and
   the scanner further comprises third and fourth magnetic poles affixed to the support at a second angular position with respect to the axis, said second angular position being different from the first angular position, said third magnetic pole being arranged on the first side of the annular disk, said fourth magnetic pole being arranged on the second side of the annular disk opposite the third magnetic pole.

7. An X-ray scanner as claimed in claim 6, characterized in that the annular disk consists of aluminum.

* * * * *